United States Patent [19]

Michas

[11] Patent Number: 4,674,123
[45] Date of Patent: Jun. 16, 1987

[54] TEST BENCH FOR THE ADJUSTMENT OF ELECTRO-ACOUSTIC CHANNELS AND PARTICULARLY OF DEVICES FOR AUDITORY CORRECTION

[76] Inventor: Frederic Michas, 86 Avenue Trespoey, 64000 Pau, France

[21] Appl. No.: 614,827

[22] Filed: May 25, 1984

[30] Foreign Application Priority Data

May 27, 1983 [FR] France .................. 83 09120

[51] Int. Cl.$^4$ .......................................... H04R 29/00
[52] U.S. Cl. ........................................ 381/60; 381/68
[58] Field of Search ...................... 381/60, 68; 73/585, 73/645; 128/746

[56] References Cited

U.S. PATENT DOCUMENTS

| | | | |
|---|---|---|---|
| 3,922,506 | 11/1975 | Frye . | |
| 3,949,735 | 4/1976 | Klar et al. | 73/585 |
| 4,079,198 | 3/1978 | Bennett | 73/585 |
| 4,095,057 | 6/1978 | Power et al. . | |
| 4,099,035 | 7/1978 | Yanick . | |
| 4,251,686 | 2/1981 | Sokolich | 73/585 |
| 4,289,143 | 9/1981 | Canavesio et al. | 73/585 |
| 4,459,996 | 7/1984 | Teele | 73/585 |

FOREIGN PATENT DOCUMENTS 0010169 4/1980 European Pat. Off. .

OTHER PUBLICATIONS

"The Production Model of the Automatic A.F. Response Curve Tracer" *Journal of the British Institution of Radio Engineers*, May, 1951, G. L. Hamburger, pp. 165–201.

*Primary Examiner*—Forester W. Isen

[57] ABSTRACT

Test bench for the adjustment of electro-acoustic channels and particularly auditory corrective apparatus.

The present invention has for its object a test bench for the adjustment of electro-acoustic channels and particularly auditory corrective apparatus (1) such that the latter restores with fidelity the tone and volume of perceived sounds, and restores these sounds with greater or lesser intensity as a function of the hearing of the person who is hard of hearing.

The test bench is characterized essentially in that it is constituted:

by several sources (2) for the production of electric signal, by at least one means (3) for transformation of the electric signal into a sonic signal, said sonic signal being received by the apparatus (1), by at least one assembly of means 4 to model an auditory corrective apparatus suitable for the person who is hard of hearing, by at least one means (5) to transform into an electric signal the sonic signal received by the apparatus, by at least one means (6) to transform into an electric signal the sonic signal emitted by the apparatus, by a means (7) to visualize the electric signals delivered by the means (4), the means (5) and the means (6), which is to say to visualize the sonic signal received by the apparatus, the response of said apparatus and the response of the model and by memorization means for the visualized electric signals.

18 Claims, 8 Drawing Figures

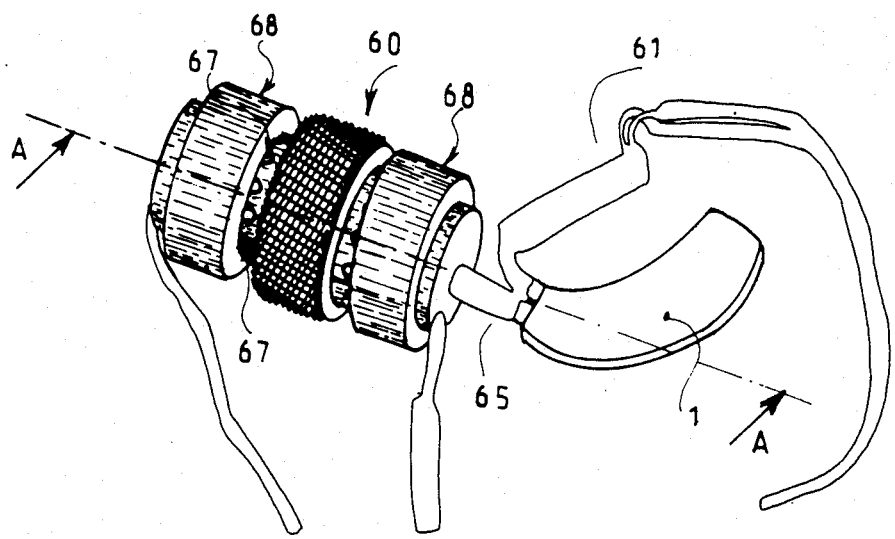
FIG. 5
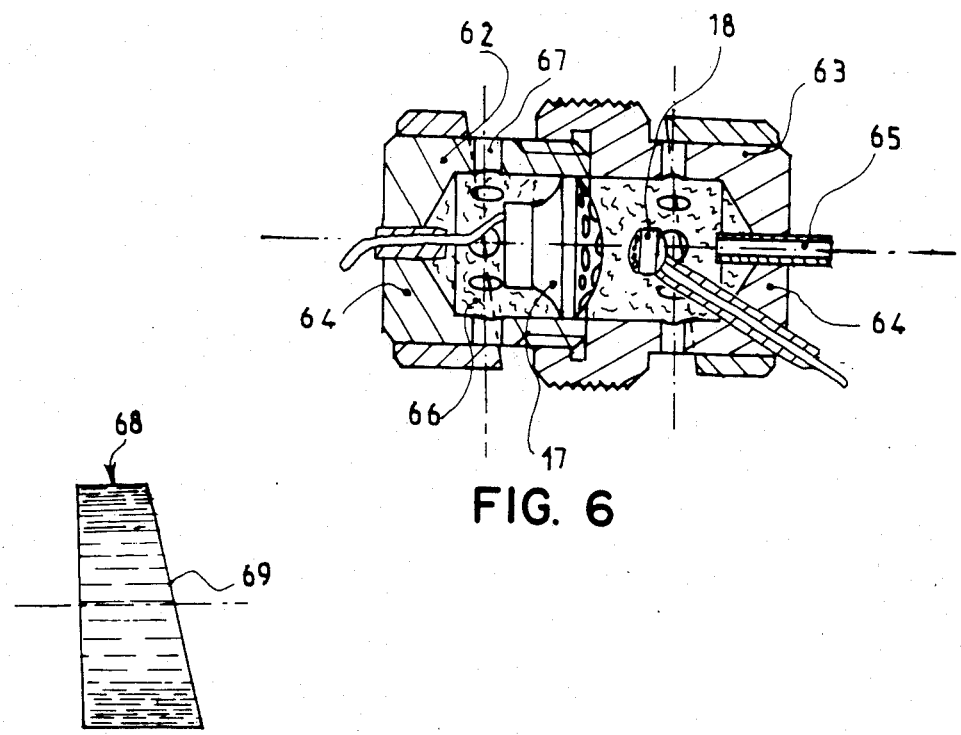
FIG. 6
FIG. 7

TEST BENCH FOR THE ADJUSTMENT OF ELECTRO-ACOUSTIC CHANNELS AND PARTICULARLY OF DEVICES FOR AUDITORY CORRECTION

The present invention has for its object a test bench for electro-acoustic channels and particularly for apparatus for use by the hard of hearing.

To reestablish normal hearing in the hard of hearing with the aid of auditory corrective apparatus it is necessary in the first instance to correct the distortions which this type of apparatus imparts to the reproduction of sounds of the audible spectrum and in the second instance to adapt this apparatus to the hearing of the patient.

In the first instance this type of apparatus must therefore be adjusted so as to amplify each frequency of the sonic spectrum in an identical way and therefore must be adjusted so as not to reproduce certain of the frequencies with increased intensity.

Moreover, this type of apparatus must reproduce fairly faithfully sharp sounds and thus must have a good response to impulse signals.

It should also be noted that the analysis of the response of this type of apparatus to squared signals of determined frequency is useful to inform those skilled in the art of the functioning of the channel and particularly of the response to transitory phenomena such as peaks of resistance. At this stage, to facilitate adjustment of the apparatus, it is desirable that all the modification of the latter so as to improve its defects, should be immediately perceptible to a person skilled in the art.

Moreover, it is necessary that a person skilled in the art be able to compare at each instant the response curve of the apparatus to the sonic signals perceived by said apparatus.

When a person skilled in the art has performed these various adjustments he can adapt the auditory corrective apparatus to the hearing of the patient. In the first instance, the person skilled in the art, with the help of the patient, determines the regions of the sonic spectrum for which an attenuation is to be achieved and the regions of the sonic spectrum which must be subjected to amplification, the aim being to restore the most normal hearing possible.

Moreover, at this stage of the adaptation of the apparatus it is desirable to expose the patient to the sounds of the natural environment so as to refine the adjustment.

In conclusion it will be understood that the restoration of normal hearing in one who is hard of hearing depends in large measure on the quality of the adjustment effected on the auditory corrective apparatus.

The present invention therefore has for its object a test bench for electro-acoustic channels and particularly for auditory corrective apparatus permitting facilitating the adjustment of this type of apparatus.

To this end, the test bench according to the present invention for adjusting electro-acoustic channels and particularly auditory corrective apparatus, so that the latter will restore with fidelity the tone and volume of the sound perceived and restore these sounds with greater or lesser intensity as a function of the hearing of the hard of hearing person, is constituted:

by several sources for the production of an electric signal, by at least one means for the transformation of this electric signal into a sonic signal, said sonic signal being received by the apparatus, by at least one assembly of means to model an auditory corrective apparatus suitable for the hard of hearing person, by at least one means to transform into an electric signal the sonic signal entering the apparatus, by at least one means for transforming into an electric signal the sonic signal leaving the apparatus, by means to display these different electric signals and by means to memorize the displayed electric signals.

According to another characteristic of the invention, the signals are visualized according to a linear scale such that the defects or distortions, introduced by the apparatus into this reproduction of the sounds, can be perceived in their true value.

Other advantages and characteristics of the invention will appear from a reading of the description of a preferred embodiment given by way of non-limitative example with reference to the accompanying drawings in which:

FIG. 5 is a perspective view of an acoustic coupler of the test bench according to the invention.

FIG. 6 is a cross-sectional view on the line AA of FIG. 5.

FIG. 7 is a side view of a sleeve of the acoustic coupler according to FIG. 5.

Figure 1:
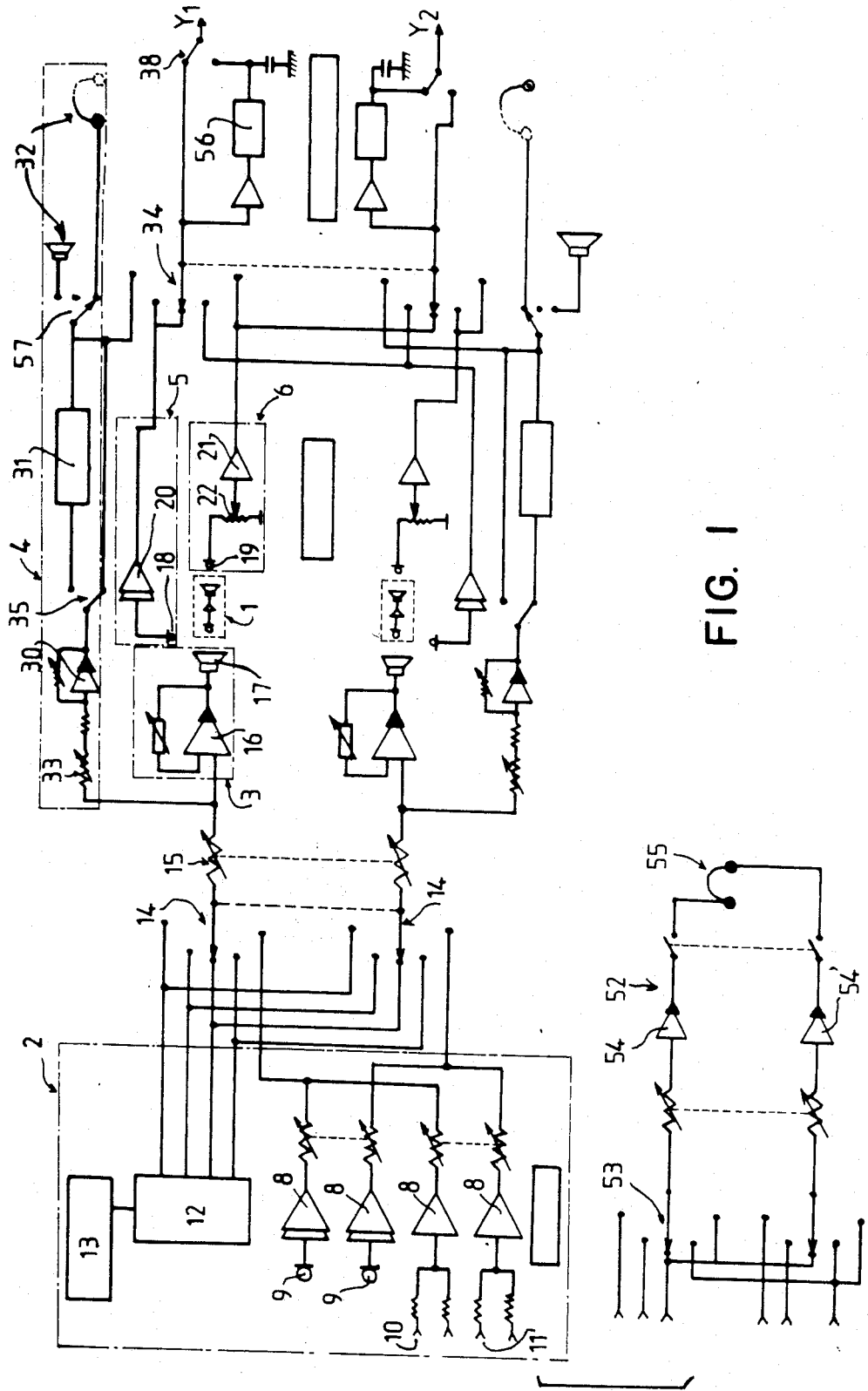
FIG. 1 is an overall diagram of the test bench according to the invention.
Figure 2:
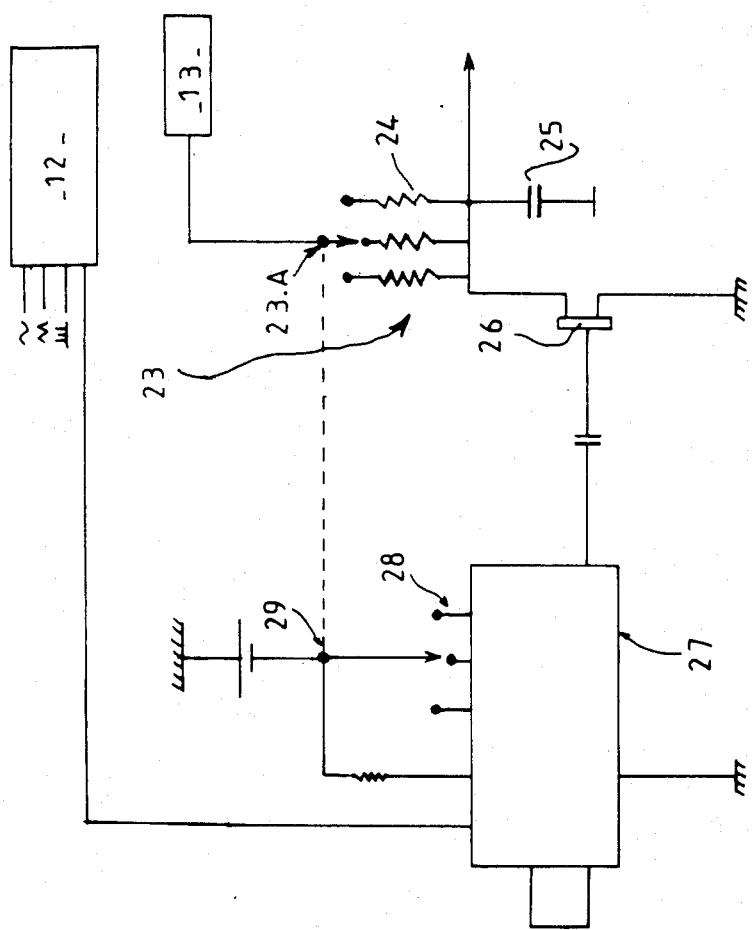
FIG. 2 is an electronic diagram of the time base of the visualization means of the test bench.
Figure 3:
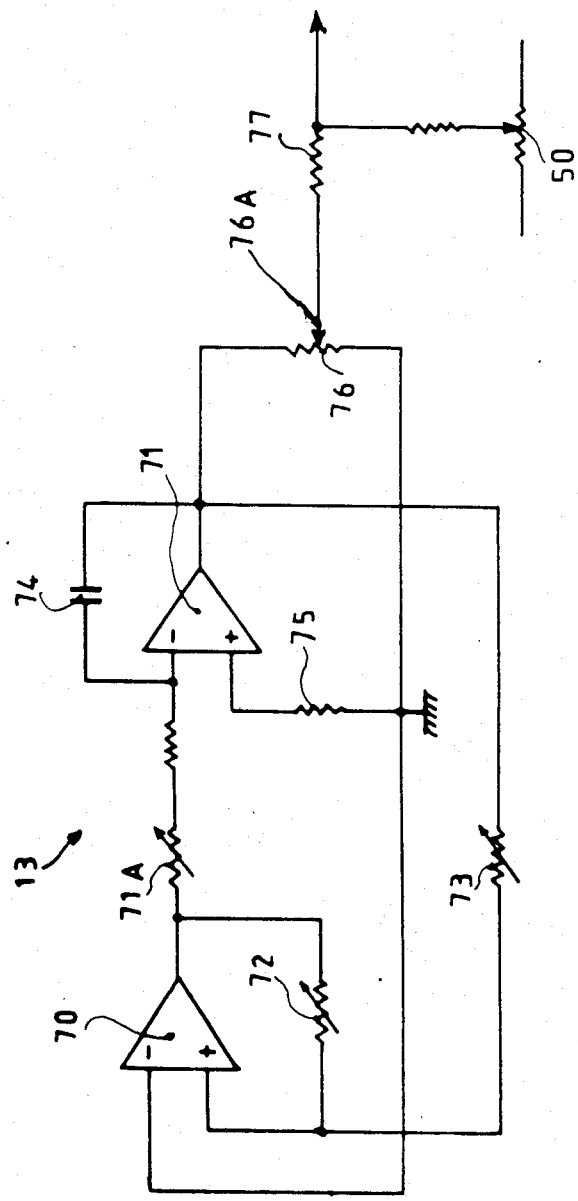
FIG. 3 is an electronic diagram of the scanning generator of the test bench.

As shown, the test bench according to the invention for the adjustment of electro-acoustic channels and particularly apparatus 1 for auditory correction such that the latter will restore with fidelity the tone and volume of the sounds perceived and will restore the sounds with a greater or lesser intensity as a function of the hearing of the hard of hearing person, is constituted:

by several sources 2 for the production of an electric signal, by at least one means 3 for the transformation of the electric signal into a sonic signal, said sonic signal being received by apparatus 1, by at least one assembly of means 4 to model the right auditory corrective apparatus to the hard of hearing person, by at least one means 5 to transform into an electric signal the sonic signal which is emitted by means 3 and therefore received by apparatus 1, by at least one means 6 to transform into an electric signal the sonic signal emitted by the apparatus, by at least one means 7 for displaying the different electronic signals, and by at least means for memorization of these different displayed electric signals.

Thus one skilled in the art will be able to perceive the defects and distortions of the apparatus thereby to facilitate its adjustment, and by comparison of the memorized response of the model with the corrected response of the apparatus will be able to adjust said apparatus to the hearing of the patient.

According to a preferred embodiment the sources 2 are constituted by at least one means generating an audio frequency signal and by at least one means generating a squared signal, a triangular signal, a train of impulses, and a sinusoidal signal of fixed or variable frequency.

According to the preferred embodiment, the test bench is provided with several means each generating an audio frequency signal. As can be seen in FIG. 1 each of these means is constituted by an amplification stage 8 excited by a microphone 9 or by a radiophonic receiver 10 or by a reader 11 of a prerecorded magnetic tape.

Preferably, the squared signals, triangular signals, the train of impulses and the sinusoidal signal of fixed or variable frequency are delivered by a functions generator 12 known per se. Means 13 is associated with the functions generator 12 to control the frequency of the signals emitted by this generator.

This means 13 is a generator which can deliver either a continuous voltage of adjustable amplitude or else a cyclicly increasing and decreasing voltage.

The generator 12 for the production of squared signals, triangular signals, impulse trains and the sinusoidal signal comprises four outputs each dedicated to one of these signals.

One of the signals delivered by this generator or by the audio frequency sources is selected to excite the means 3 for the production of the sonic signal received by the corrective apparatus or to excite the means 4.

To this end, between the sources 2 and the means 3 and 4 is disposed a multiposition selector 14 known per se.

Moreover, to adjust the volume of the signals in the means 3 and 4 a potentiometer 15 is disposed between the multipositions selector 14 and these means 3 and 4.

As needed, one skilled in the art will select one of these audio frequency signals or the squared signals, triangular signals, the train of impulses, or the sinusoidal signal.

The audio frequency signals are for example selected when the person skilled in the art wishes to create a model of apparatus such that the squared signals, triangular signals, sinusoidal signals, and the train of impulses are preferably selected when he proceeds to the adjustment of the apparatus to reduce the defects or the distortions.

The visualized form of the response of the apparatus to the squared signal, whose frequency is preferably equal to 200 Hz, is representative of the overall functioning thereof.

It is particularly to be noted that the observation of the form of the response permits the detection of the resident peaks and gives precision to the responses of the apparatus to transitory phenomena.

The visualized form of the response of the apparatus to the train of impulses is respresentative of the reproduction of the sharp noises.

By observation of this form of response, the person skilled in the art will be able to determine if the apparatus restores this type of noise with or without slight resistance.

Preferably, the sinusoidal signal is regularly variable, which is to say that the frequency of this signal increases and decreases in a cyclic manner. This variation of frequency of the sinusoidal signal is controlled by the generator 13 which produces for this purpose a triangular signal inserted in the generator 12.

It is to be noted that the frequency variation of the signal is effectuated at constant amplitude and that this amplitude may be adjusted by the operator. Preferably the frequency of the sinusoidal signal is variable between 20 Hz and 20,000 Hz.

The observation of the response of the apparatus to this signal permits detecting the variations of amplitude and the excess current in a frequency band under study.

Moreover, the observation of the symmetry of the envelope of the shape of the response permits detecting any clipping of the amplifier of the corrective apparatus.

It is also to be noted that the functions generator may deliver a sinusoidal signal of fixed frequency.

To this end the means 13 delivers a continuing voltage whose value controls the frequency of the signal emitted by the generator 12. The selective signal excites the means 3, and the means 4.

The means 3 is constituted by a power amplifier 16 and by an electro-acoustic transducer 17 for example a loudspeaker. The amplifier 16 and the loudspeaker 17 are of the type of those having good frequency response so as not to produce any distortion during transformation of the electric signal into a sonic signal.

By way of non-limiting example, the amplifier 16 is an integrated circuit of the type "LM324" having two transistors mounted in push-pull and the loudspeaker is of the type sold by "Sony" under the mark "MDR3 WALKMAN".

The sonic signal emitted by the loudspeaker 17 is received on the one hand by the microphone of the apparatus and on the other hand by the means 5. This means transforms the sonic signal into an electric signal which thus can be displayed by the means 7.

The means 5 and 6 are constituted each by a microphone and by an amplification stage excited by this microphone.

The electric signal is received at the output of the amplifier and is inserted in the display means 7.

The loudspeaker 17 is acoustically connected to the microphone 18 of the means 5 and the microphone of the auditory corrective apparatus and the loudspeaker of this apparatus is connected acoustically to the microphone 19 of the means 6.

To this end, the test bench comprises a first acoustic coupler 60 cooperating with the loudspeaker 17, the microphone 18 and the microphone of the apparatus 1 and a second acoustic coupler 61 coacting with the loudspeaker of said apparatus 1 and the microphone 19 of means 6.

The coupler 60 as can be seen in FIGS. 5 and 6 is constituted by two tubular chambers 62 and 63 each comprising a base 64 and a screw-threaded opening for screwing one onto the other. In chamber 62 is disposed the loudspeaker 17 and in chamber 63 the microphone 18. The base 64 of chamber 62 is traversed by an opening for the passage of the electric wires to the loudspeaker 17 and the base 64 of chamber 63 is traversed by two openings for the passage of electric wires of the microphone 18 and for the passage of a flexible tube 65 acoustically connecting chamber 63 to the microphone of apparatus 1.

In chambers 62 and 63 is introduced foam 66 or any other analogous material for avoiding all acoustic resonance phenomena. To adjust acoustically the acoustic coupler and particularly the sonic level of deep tones, each chamber 62 and 63 is provided with a series of angularly spaced transverse openings 67 provided in its cylindrical wall and with a sleeve 68 enclosing with slight friction said wall. This sleeve can more or less obstruct the orifices 67. Preferably the edge 69 of the sleeve which overlies the openings is inclined relative to the plane perpendicular to the axis of said sleeve. This arrangement permits obstructing certain orifices 67 and exposing others.

The acoustic coupler 61 is constituted by a flexible tube terminating in two end ferrules for connecting it on the one hand to the ferrule of the apparatus 1 and on the other hand to the microphone 19 of the means 6. The means 5 and 6 are constituted by members known per se, having good frequency response to avoid any distortion in the transformation of the sonic signal into an electric signal.

By way of non-limiting example, the microphone 18 of means 5 and the microphone 19 of means 6 are sold by "LEM" under the mark "EM 76". Amplifier 20 of means 5 and the amplifier of means 6 are constituted each by an integrated circuit "LM324".

The simplicity of construction of means 5 and 6, the latter having no corrective apparatus for the electric signal, results in a reduction of the response time of these means. As can be seen in FIG. 1, the means 6 is provided between the microphone 19 and the amplifier 21 with a potentiometer 22 to adjust the signal level inserted in this amplifier and consequently the electric signal level inserted in the means display 7.

The two electric signals present respectively at the output of means 5 and the output of means 6 are representative of the sonic signal inserted in the apparatus and of the sonic signal delivered by the latter which is to say the response of this apparatus. Preferably these two signals are simultaneously displayed which facilitates the comparison of them.

To this end, the display means 7 comprises two inputs respectively designated Y1 and Y2. This display means is preferably constituted by a double trace cathode tube associated with an electronic circuit ensuring its functioning which is to say essentially the control of the displacement of the luminous dots. These inputs Y1 and Y2 are those of the stages controlling the vertical scanning of the luminous dots. These two inputs being directly associated with the means 5 and 6 the signals emitted by these means are represented on a linear scale which permits a correct evaluation of the defects or distortions. Preferably the cathode tube is of the type of those having weak remanence. According to another embodiment the display means may be constituted by a video screen.

This characteristic, combined with the characteristic of means 5 and 6 which have low response times, results in that the modifications of the apparatus with a view to reducing defects are immediately displayed. Moreover, this characteristic is reinforced during use of the variable frequency sinusoidal signal. Thus, as is known, the frequency of this type of signal increases progressively and decreases progressively. As a result, the path of the luminous dot when the frequency decreases will be superposed exactly on the path of the luminous dot when the frequency increases.

The image of the displayed signals is therefore particularly stable and the modifications of the apparatus with a view toward reducing the distortions are therefore visualized in real time. As the horizontal scanning of the luminous dot should be progressive in one direction as well as the other during utilization of the variable frequency signals the base time circuit 23 of the display means 7 provides a triangular signal whose amplitude increases and decreases conjointly as the frequency of the variable frequency signal. It will be evident that during the use of non-variable frequency signals the base time circuit 23 of the display means 7 provides sawtooth signals.

According to a preferred embodiment the base time circuit is fed by the generator 13 which controls the generator 12. This base time circuit 23 is controlled by display means 27 of the signals following two or several periods. The base time circuit 23 is constituted by at least one resistance 24 and by a condenser 25 charged by said resistance. At the terminal of this condenser is withdrawn the base time signal to be inserted in the display means 7.

The resistance 24 receives from the generator 13 the charge voltage of the condenser 25 to adjust the amplitude of the voltage to the terminals of the latter as a function of the frequency of the signal visualized by the means 7. Thus the screen of means 7 may be linearly graduated, each of the graduations corresponding to one frequency. The scanning generator 13 is constituted by two amplifiers 70 and 71. Amplifier 70 comprises a counter-reaction circuit constituted by a variable resistance 72. This resistance is connected to the non-commutating input of this amplifier and to its output. The non-commutating input of this amplifier is connected by a variable resistance 73 to the output of amplifier 71. The commutating input of amplifier 70 is connected to the ground. The output of this amplifier is connected to the non-commutating input of the amplifier 71 by a variable resistance 71A which controls the scanning speed and thus the variable frequency speed. Amplifier 71 also comprises a counter reaction circuit constituted by a condenser 74. The non-commutating input of this amplifier is connected to ground by means of a resistance 75. The output of amplifier 71 is connected to ground by means of an adjustable resistance 76. The slide 76A of this resistance is connected by means of a resistance 77 to the generator 12 and to the base time circuit. For adjusting the resistance 76 the operator adjusts the size of the variable frequency band and the width of scanning.

Preferably, on the voltage delivered by resistance 77, there is superposed a continuous voltage controllable by a potentiometer 50. This potentiometer permits adjusting the frequency from which the variation in frequency is to be effected. It will be understood that, thanks to such a generator 13, the base time circuit is always fed by a voltage proportional to the frequency of the displayed signal.

With the generator 13 is associated manual controls which automatically disconnect the variation of frequency when actuated. The purpose of these controls is to permit the operator to display only one signal of fixed frequency. These controls are constituted by three switches which permit respectively the display of a signal of 500 Hz, 1,000 Hz and 4,000 Hz and by the potentiometer 50 which permits choosing a frequency between 20 Hz and 20,000 Hz.

The discharge of condenser 25 of the base time circuit is effected by an electronic switch 26. This switch 26 is constituted by a transistor for example a "2N2222" whose base receives the impulses from means 27 recited above. Under the influence of the impulses the transistor is rendered passive which discharges the condenser 25. The means 27 constituted by a counter permits the display of two or several periods of the signal to be displayed. Preferably this counter displays a number of periods equal to a multiple of two.

The number of periods to be displayed is determined by the insertion of a control voltage into one of the inputs 28 of this counter. The counter 27 receives derivatively the signal to be visualized. The counter 27 will deliver no impulse so long as the number of periods determined by the control voltage is not achieved. As will be seen, this counter comprises several inputs 28 each of which determines a number of periods to be displayed. These inputs are selected by a selector mechanism 29 known per se.

The time constant of the base time circuit 23 should be modified as a function of the number of periods to be displayed. To this end, this circuit 23 comprises several resistances 24 of different values which are selected as a function of the number of periods to be displayed by the selector 23A mechanically coupled to the selector 29.

As previously stated, the test bench is provided with means 4 to model an auditory corrective apparatus suitable for the hard of hearing person. This means 4 is excited by a signal emitted from a source 2. This means 4 is constituted by an amplifier 30, by a filter set 31 referred to as "equalizer" and by at least one electro-acoustic transducer 32 which emits sounds to be perceived by the hard of hearing person. To adjust the level of the signal inserted in the amplifier 30 a potentiometer 33 is disposed at its input. The output of this amplifier excites the equalizer 31 which excites in turn the transducer 32.

The equalizer permits attenuating or amplifying selectively one or several sonic frequency bands. Therefore with the aid of this device, one skilled in the art will be able to reestablish normal hearing in the hard of hearing person. As will be understood, this device permits analogically modeling a corrective device suitable for the hard of hearing person. The electro-acoustic transducer is constituted either by a loudspeaker and/or by a receiver. Preferably as can be seen in FIG. 1 the means 4 comprises a loudspeaker and headphones. One of these transducers is selected by a selector 57 having a neutral intermediate position. To display the response curve of the device 4 the electric signal present at the output of the equalizer is withdrawn to be inserted at one of the inputs Y1 or Y2.

As the signal emitted by the equalizer cannot be displayed simultaneously with the display of the two signals emitted by means 5 and 6, the test bench is provided with a display selector 34 known per se.

By way of example this selector is of the type of those constituted by two discs mounted on a common axle which is actuated by a pushbutton.

With each disc coacts, selectively according to its angular position, the electric contacts. One of the contacts of one of the discs receives the signal of the equalizer and one contact of one of the discs and one contact of the other receive respectively the signal emitted by means 5 and the signal emitted by means 6.

As will be understood, one of these discs is electrically connected to the input Y1 while the other is electrically connected to the input Y2. Preferably this selector, besides the signals emitted by means 5 and 6 and by the equalizer 31, permits also the display of the signals emitted by sources 2.

Preferably these signals are gathered at the output of the amplifier 30 of means 4. To derive this signal directly by the display means 7 a selector 35 is disposed between the amplifier 30 and the equalizer 31.

As will be seen from FIG. 1 the test bench may receive two auditory corrective devices.

To this end, the test bench is provided with two potentiometers 15, two means 3, two means 4, two means 5, and two means 6. The selector 34 may simultaneously select not only the electric signals emitted by means 5 and 6 associated with one apparatus 1, but also the electric signals emitted from source 2, the electric signals emitted from the two means 5, the electric signals emitted from the two means 6 and the electric signals emitted from means 4.

To adjust the corrective apparatus a person skilled in the art must know the mean gain of this apparatus when it is subjected to a variable frequency signal and the gain of the latter for a sinusoidal signal of given frequency. As is known, the gain of an electro-acoustic stage is the difference in decibels between the signal level at the input of this stage and the signal level at the output of this stage. The gain of the corrective apparatus will therefore be equal to the difference between the signal level emitted by means 5 and the signal level emitted by means 6.

To measure this gain the test bank is provided with two meters 56 of which one is connected with one disc of the selector 34 and of which the other is connected with the other disc of this selector. As the signals emitted by means 5 and 6 associated with the same apparatus are associated each with one disc, one of these meters will indicate the signal level of means 5 and the other the signal level of means 6.

According to the embodiment, the meters 56 have a range of 20 decibels. It is thus necessary to attenuate the input signal of these meters and to provide for each three measurement ranges for example from 60 to 80 decibels, then 80 to 100 decibels, and 100 to 120 decibels. For each meter these measurement ranges are selected by a multi-position selector 36. Preferably with each of these measurement ranges is associated an electro-luminescent diode 37 to indicate to the person skilled in the art which is the measurement range he is about to select. It is to be noted that at the output of these meters the signal inserted in the latter, this signal being either the signal emitted by means 5 or else the signal emitted by means 6, is delivered according to a logarithmic scale. It is sometimes useful to a person skilled in the art to display this signal in a logarithmic form rather than a linear form.

Figure 4A:
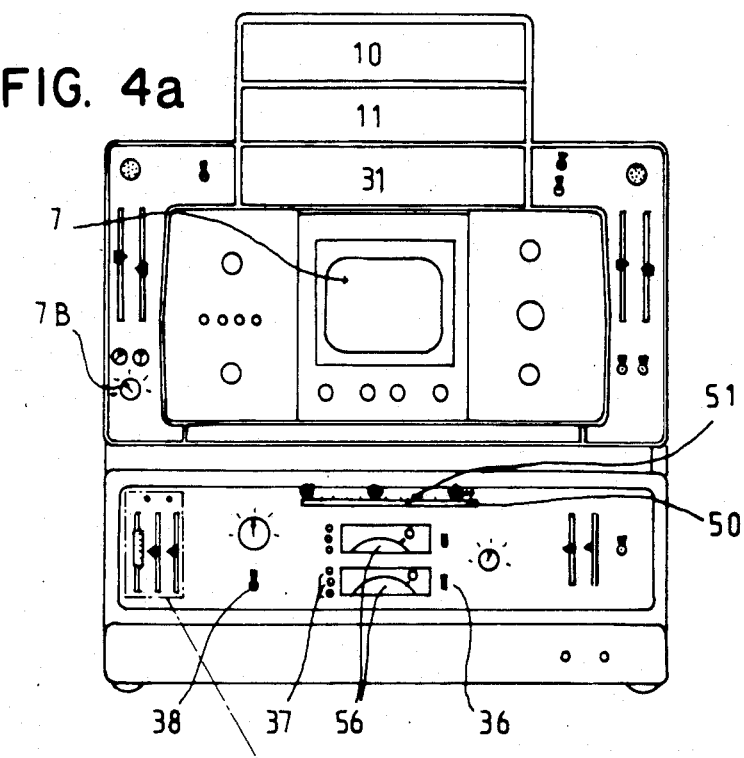
FIGS. 4A and 4B are a front view of the test bench according to the invention.
Figure 4B:
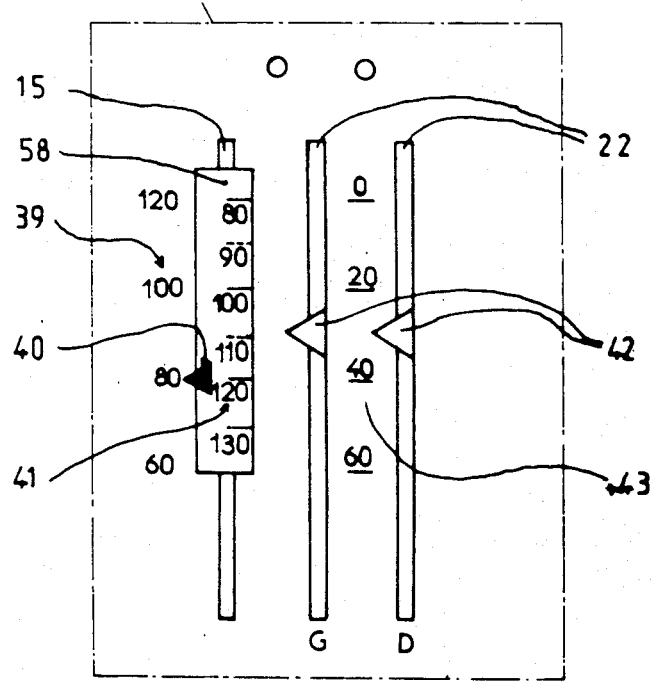

To select this logarithmic or linear mode of representation a selector 38 is associated with the input Y1 or Y2 corresponding to the means 7. This selector has two selector positions, either the logarithmic output of the corresponding meter, or else the corresponding disc of the selector 34. In FIG. 4 there is shown but a single potentiometer 15 although the test bench according to the illustrated embodiment receives two devices 1.

Referring to FIG. 1, it will be seen that this potentiometer 15 is in fact a double potentiometer comprising thus two tracks adjusting the level of the input signal of the means 3 and 4. It is quite evident that this potentiometer is adapted to deliver two signals of equal level. The two potentiometers 22 shown in FIG. 4 are each associated with a corrective device 1. As it is necessary to attentuate the signal emitted by means 6 with potentiometer 22 it is necessary in order to measure the gain of the apparatus to take account of this attentuation.

To facilitate this measurement the potentiometers 15 and 22 are disposed beside each other, comprising each an index and slide in front of a graduated scale. Moreover the manipulating rod of the potentiometer 15 comprises a graduated scale 58 opposite which the indices of the potentiometers 22 are disposed. The graduated scales of the potentiometers 15 and 22 and the graduations of the scale 58 extend in the same direction and are so provided as to indicate whatever is the position of the potentiometers, the signal level perceived by the apparatus, the signal level emitted by the apparatus and the attentuation level and thus the gain of the apparatus.

As can be seen in FIG. 4, the graduated scale 39 of the potentiometer 15 indicates the values increasing upwardly. These values are relative to the level of the signal perceived by the device. The adjustment of the signal level is effective to dispose an index 40 opposite a graduation of the scale 39. This index 40 is carried by the scale 58. The graduations 41 of the scale 58 are related to the level of the signal emitted by the apparatus 1 The values marked on this scale increase downwardly. Opposite one of the graduations of the graduated scale 58 will be disposed two indices 42 carried respectively by each potentiometer 22. Moreover these graduated indices will be disposed each opposite a graduated scale relative to the level of attenuation of the signal emitted by the means 6 and thus to the gain of the apparatus. The values marked on this scale increase downwardly.

For an example will now be described the use of the various graduated scales as well as the meters. For example a person skilled in the art subjects the apparatus to a sonic signal at a level of 80 decibels. He selects first the measurement range by means of the selector 36. For example he selects the measurement range between 60 and 80 decibels. By then acting on the potentiometer 15 he will bring the index 40 opposite the graduation marked "80" of the graduated scale 39.

The pointer of the meter measuring the signal level perceived by the apparatus will swing and will come opposite the graduation marked "0" of said meter. By means of one of the potentiometers 22 which adjusts the attentuation level of the signal emitted by the apparatus, the person skilled in the art swings the arrow of the second meter for a measurement of this signal opposite the graduation "0". The reading of the gain of the apparatus will be indicated by the index 42 and by the graduated scale 43.

Moreover this index, which is disposed opposite the graduations 41 of the scale 58 indicates the signal level of the output. It is quite evident that the person skilled in the art has first adjusted the measurement range of the second meter. When the person skilled in the art uses variable frequency signals he can measure only the mean gain. However he is interested to know the gain of the apparatus at a given frequency. In this case, the person skilled in the art acts on the means 22 so as to apply to the functions generator a continuous voltage whose amplitude, which controls the frequency of the signal, is controlled by potentiometer 50.

Potentiometer 50, as can be seen in FIG. 4, is disposed below the cathode tube and is operated horizontally. This potentiometer comprises an index which slides opposite a graduated scale 51 relative to the frequency of the sinusoidal signal.

As previously stated, the test bench is provided with means to memorize particularly the response of the model of corrective apparatus. For example this means could be constituted by a photographic device. By comparison between the memorized curve of the apparatus model and the response of the apparatus, the person skilled in the art will be able to proceed with a view to adapting said apparatus to the hearing of the patient.

Moreover, thanks to the memorization of the response of the apparatus model, the person skilled in the art will be able to follow the evolution of the deafness of the hard of hearing person and will also be able to adjust the corrective apparatus, without the presence of the hard of hearing person. Preferably the test bench may be provided with a printer which writes the data useful for the operator.

The test bench according to the invention may preferably comprise a numbering of the values obtained for example by an analogic numeric converter permitting the display of the frequency values, of the decibels and of the percentage of distortion. The test bench is also provided with means 52 usable by the person skilled in the art which permits listening to the various signals. These means are constituted by a listening selector 53 which selects one of the signals emitted by the different means of the test bench by amplification stages 54 and by electro-acoustic transducers 55 usable by the operator or by the patient.

The test bench according to the present invention is more particularly adapted for the adjustment of auditory corrective apparatus but it follows that it can be used in the adjustment of all electro-acoustic channels.

It will be understood that the present invention is not limited to the embodiment previously described but on the contrary includes all variations.

I claim:

1. Test bench for the adjustment of an electro-acoustic auditory correction apparatus, said apparatus restoring with fidelity the tone and volume of sound with appropriate intensity as a function of the frequency of response of a hearing impaired person, said bench comprising: several sources (2) for the production of at least one first electric signal, at least one means (3) to transform said first electric signal into a first sonic signal, said first sonic singal being received by at least one means (5) to directly transform it into a second electric signal and said first sonic signal being received in said auditory correction apparatus (1), said auditory correction apparatus transforming said first sonic signal into a second sonic signal, at least one means (6) to transform said second sonic signal into a third electric signal, at least one assembly (4) to model said auditory correction apparatus in a manner suitable with respect to the response of a hearing impaired person, said assembly delivering a fourth electric signal in response to said first electric signal, means to display said second, third and fourth electric signals, and means to record said display.

2. Test bench according to claim 1 in which said displayed electric signals are displayed on a linear scale.

3. Test bench according to claim 1 in which said sources (2) comprise at least one means generating an audio frequency signal and at least one means (12) generating a squared signal, a triangular signal, a train of impulses and a sinusoidal signal of fixed or variable frequency.

4. Test bench according to claim 1 comprising a means (12) which generates electric signals and a display unit (7) comprising a time base circuit 23 further comprising a sweeping generator (13) which controls said time base and said means to generate electrc signals (12).

5. Test bench according to claim 4 wherein the sweeping generator (13) produces a triangular signal to control the frequency variation of the signal.

6. Test bench according to claim 1 in which said first electric signal is of constant amplitude and variable frequency such that the frequency of this signal increases and decreases in a cyclic manner.

7. Test bench according to claim 1 comprising a display means (7) provided with a cathode tube which has low remanence and that the means (6) to transform the second sonic signal has short response time such that the corrective effects of the apparatus to reduce defects or distortions will be immediately displayed.

8. Test bench according to claim 1, wherein said transforming means (3) comprises a loudspeaker (17), said transforming means (5) comprisies a microphone (18), said apparatus (1) comprises a microphone and a loudspeaker, and said transforming means (6) comprises a microphone (19), wherein a first acoustic coupler (60) acoustically couples said loudspeaker (17), said microphone (18) and the microphone of the apparatus (1), and wherein a second acoustic coupler acoustically couples said loudspeaker of the apparatus and said microphone (19).

9. Test bench according to claim 8 in which the coupler (60) comprises two tubular chambers (62) and (63) containing the loudspeaker (17) and the microphone (18), each chamber comprising a base (64) and a threaded mouth for screwing into the other chamber.

10. Test bench according to claim 9 wherein the chambers (62) and (63) are filled with foam.

11. Test bench according to claim 9 further comprising a tube acoustically coupling the chamber (63) to the microphone of the apparatus (1).

12. Test bench according to claim 9 in which each chamber (62) and (63) is provided with a series of transverse openings (67) angularly provided in its cylindrical wall and with a movable sleeve (68) surrounding with slight friction said wall so as to obscure a selected number of said openings.

13. Test bench according to claim 1 further comprising a potentiometer (15) to adjust the signal volume of the first electric signal of sources (2) in the means (3) and (4).

14. Test bench according to claim 13 wherein said means (6) comprises a microphone (19), an amplifier (21) and a potentiometer (22) disposed between the microphone and the amplifier.

15. Test bench according to claim 14 wherein the potentiometers (15) and (22) are disposed side-by-side, each potentiometer comprises an index, each potentiometer slides next to a graduated scale such that the potentiometer (15) comprises a graduated scale (58) facing which are the indices of the potentiometers (22).

16. Test bench according to claim 15 wherein the graduated scales of the potentiometers (15) and (22) extend in the same direction and are arranged so as to indicate the signal level of the first sonic signal, the signal level of the second sonic signal and the gain of the apparatus no matter what the position of said potentiometers.

17. Test bench according to claim 1 further comprising display selector (34).

18. Test bench according to claim 1 wherein said display means comprises a time base circuit such that said time base circuit is fed with voltage by a scanning generator (13).

* * * * *